United States Patent [19]

Selsted et al.

[11] Patent Number: 5,422,424
[45] Date of Patent: Jun. 6, 1995

[54] ANTIBIOTIC CRYPTDIN PEPTIDES AND METHODS OF THEIR USE

[75] Inventors: Michael E. Selsted, Irvine, Calif.; Andre J. Ouellette, Lynn; Samuel I. Miller, Brookline, both of Mass.

[73] Assignees: The Regents of the University of California, Oakland, Calif.; The Shriner's Hospital for Crippled Children, Tampa, Fla.; The General Hospital Corporation, Boston, Mass.

[21] Appl. No.: 930,649

[22] Filed: Aug. 14, 1992

Related U.S. Application Data

[63] Continuation-in-part of Ser. No. 889,020, May 26, 1992, abandoned.

[51] Int. Cl.⁶ .............................. C07K 7/10
[52] U.S. Cl. ................. 530/324; 530/806
[58] Field of Search ........ 530/324, 334, 387.9, 530/806; 514/12, 21; 436/503, 547, 518, 548

[56] References Cited

U.S. PATENT DOCUMENTS

| | | | |
|---|---|---|---|
| 3,714,140 | 1/1973 | Sipos | 530/334 |
| 4,543,252 | 9/1985 | Lehrer et al. | |
| 4,659,692 | 4/1987 | Lehrer et al. | |
| 4,705,777 | 11/1987 | Lehrer et al. | |
| 5,032,574 | 7/1991 | Wilde et al. | |
| 5,191,015 | 3/1993 | Sheppard et al. | 530/334 |

OTHER PUBLICATIONS

Eisenhauer, Patricia B. et al. "Cryptdins: Antimicrobial Defensins of the Murine Small Intestine." Infection and Immunity. 60:3556–3565 (1992).

Ouellette et al, 1989. Developmental regulation of cryptdin, a corticostatin/definsin precursor mRNA in mouse small intestinal crypt epithelium. J. Cell Biol. 108:1687–95.

Ouellette et al, Jun. 1992. Purification and primary structure of murine cryptdin-1, a Paneth cell defensin. FEBS Lett. 304:146–8.

Selsted et al, Aug. 1992. Enteric defensins: antibiogic peptide components of intestinal host defense. J Cell Biol. 118:929–36.

Daher et al, 1988. Isolation and characterization of human defensin cDNA clones. Proc. Natl. Acad Sci. 85:7327–31.

Ganz et al, 1989. The structure of the rabbit macrophage defensin genes and their organ-specific expression. J. Immunol. 143:1358–65.

Ganz et al, 1985. Defensins. Natural peptide antibiotics of human neutrophils. J. Clin. Invest. 76:1427–35.

Maurer et al, 1980. Proteins and polypeptides as antigens. Meth. Enzymol. 70:49–70.

Stewart et al, 1984. *Solid Phase Peptide Synthesis.* Pierce Chemical Co., Rockford. pp. 90–91.

Ouellette, Andre J. and Lualdi, John C. "A Novel Mouse Gene Family Coding for Cationic, Cysteine-rich Peptides." J. Biol. Chem. 265:9831–9837 (1990).

Ganz, Tomas et al., "Defensins." Eur. J. Haematol. 44:1–8 (1990).

Kagan, Bruce L. "Antimicrobial Defensin Peptides Form Voltage-Dependent Ion-Permeable Channels in Planar Lipid Bilayer Membranes." Proc. Natl. Acad. Sci. USA 87:210–214 (1990).

Ouellette, Andre J. et al., "Localization of the Cryptdin Locus on Mouse Chromosome 8." Genomics 5:233–239 (1989).

*Primary Examiner*—David Saunders
*Assistant Examiner*—James L. Grun
*Attorney, Agent, or Firm*—Campbell and Flores

[57] ABSTRACT

The present invention provides substantially purified cryptdin peptides having a consensus amino acid sequence as follows:

$X_1$-C-$X_2$-C-R-$X_3$-C-$X_4$-E-$X_5$-G-$X_6$-C-$X_7$-C-C-$X_8$ wherein $X_1$ is 3–6 amino acids; $X_2$ is one amino acid; $X_3$ is 2 or 3 amino acids; $X_4$ is three amino acids; $X_5$ is three amino acids; $X_6$ is one amino acid; $X_7$ is 6 to 10 amino acids; and $X_8$ is 0 to 7 amino acids.

The invention further provides substantially purified cryptdin peptides having a consensus amino acid sequence as follows:

(Abstract continued on next page.)

ABSTRACT $X_1$-L-$X_2$-C-Y-C-R-$X_3$-C-K-$X_4$-E-R-$X_5$-G-T-C-$X_6$-C-C-$X_7$ wherein $X_1$ is one to four amino acids; $X_2$ is one amino acid; $X_3$ is three amino acids; $X_4$ is two amino acids; $X_5$ is two amino acids; and $X_6$ is six to nine amino acids; and $X_7$ is zero to seven amino acids.

The illustrated embodiments have amino acids selected from the group consisting of the following sequences:

LRDLVCYCRSRGCKGRERMNGTCRKGH-LLYTLCCR

LRDLVCYCRTRGCKRRERMNGTCRKGH-LMYTLCCR

LRDLVCYCRKRGCKRRERMNGTCRKGH-LMYTLCCR

GLLCYCRKGHCKRGERVRGTCGIR-FLYCCPR

LSKKLICYCRIRGCK-RRERVFGTCRNLFLTFVFCC

LKQCHCRKFCRPYEKAEGSCRPGLFIKR-KICCIQQWTPG

In another embodiment, the inventions provide cryptdin analogs devoid of amino acids to the N-terminal of the first cysteine.

Cryptdins are typically characterized by being naturally found in the epithelial cells of the small intestine being cationic, being between 30 and 40 amino acids in length, having 3 to 6 amino acids to the N-terminal of the first cysteine residue, exhibiting specific antimicrobial activity against intestinal pathogens and being relatively non-toxic to cells of the host organism. However, there may be diversity in these structural and functional characteristics.

The present invention provides a method for detecting inflammatory pathologies in the subject and, further, provides a method for treating an infectious process of the intestine or other organ of the patient by administering cryptdin in a physiologically acceptable medium.

1 Claim, 7 Drawing Sheets

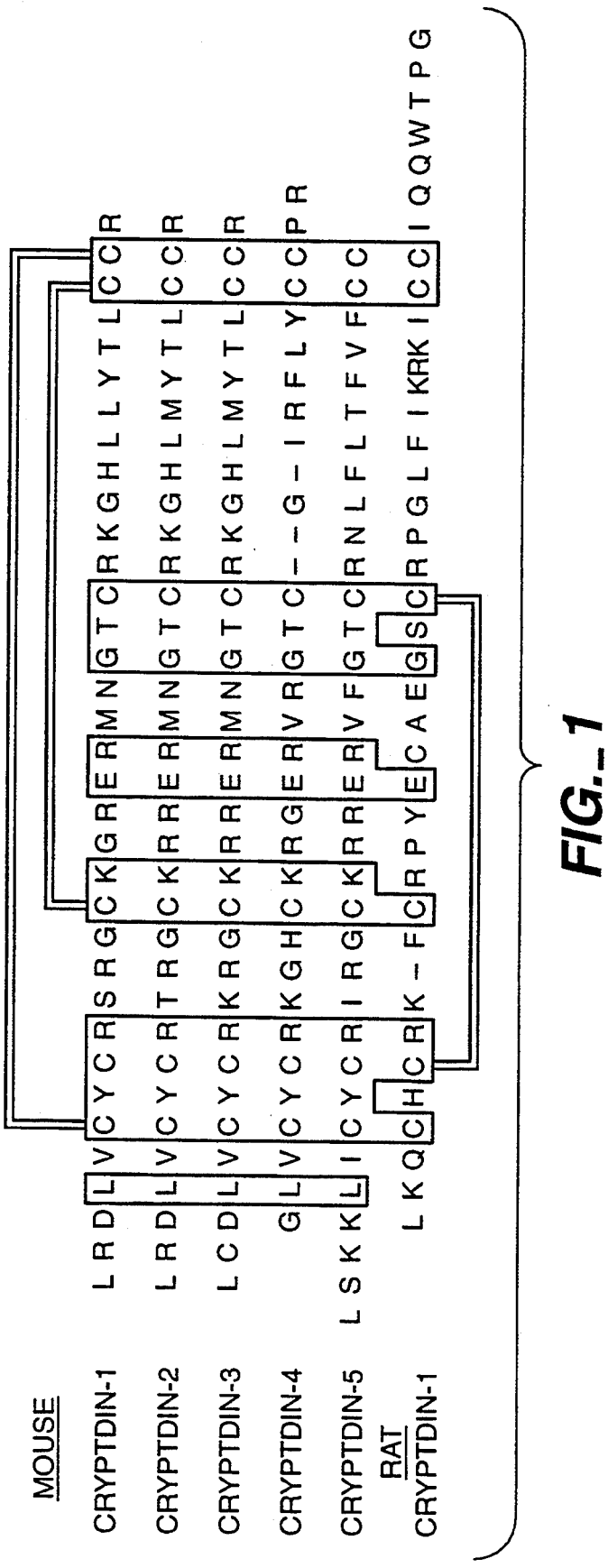
FIG._1

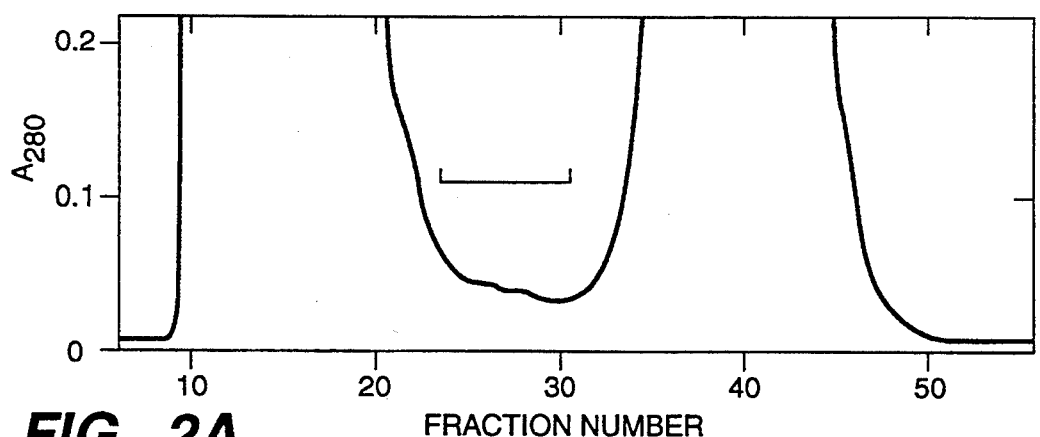
FIG._2A
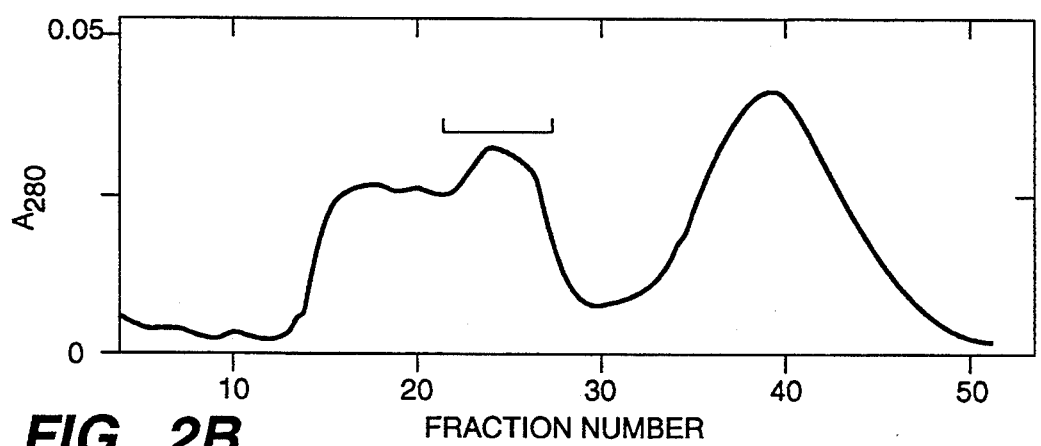
FIG._2B
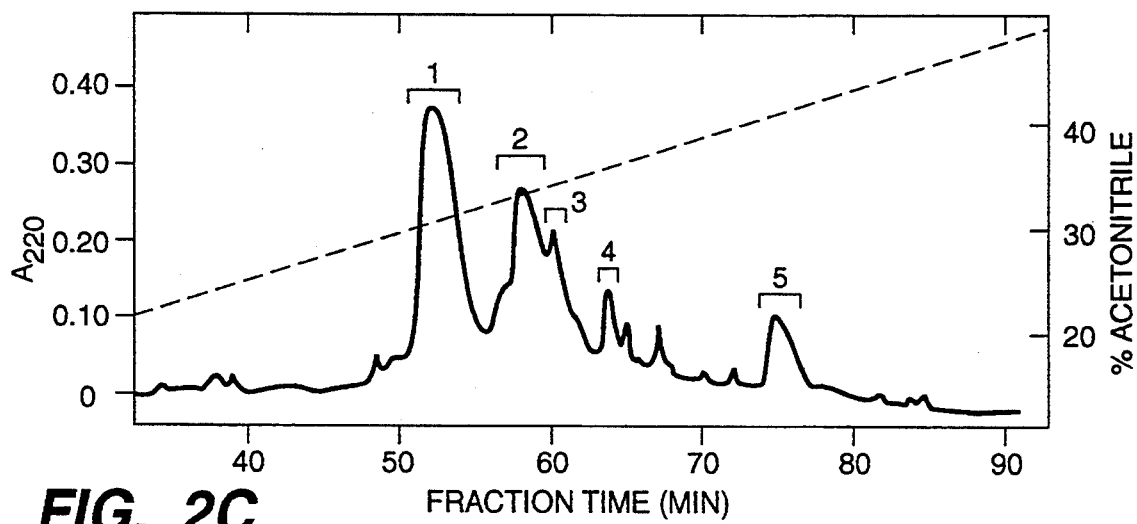
FIG._2C

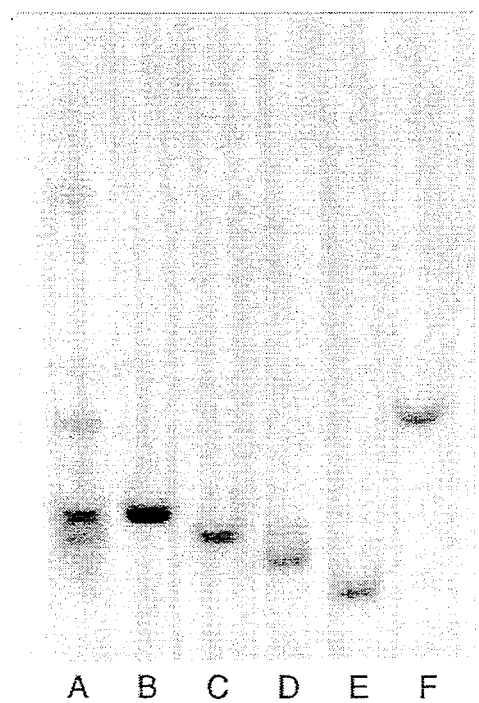
A B C D E F
FIG._3
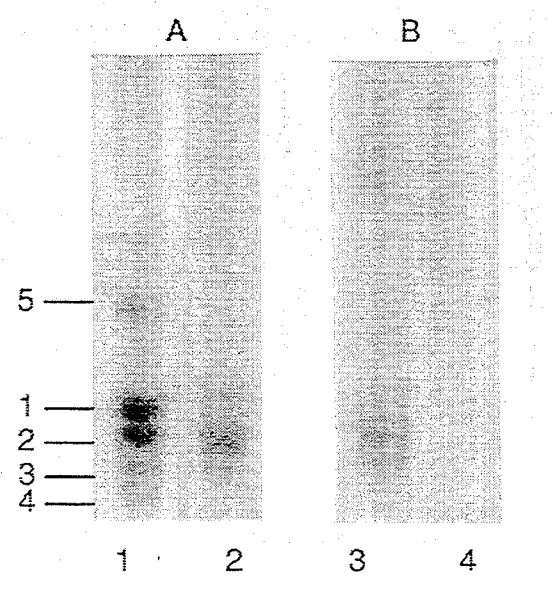
FIG._4

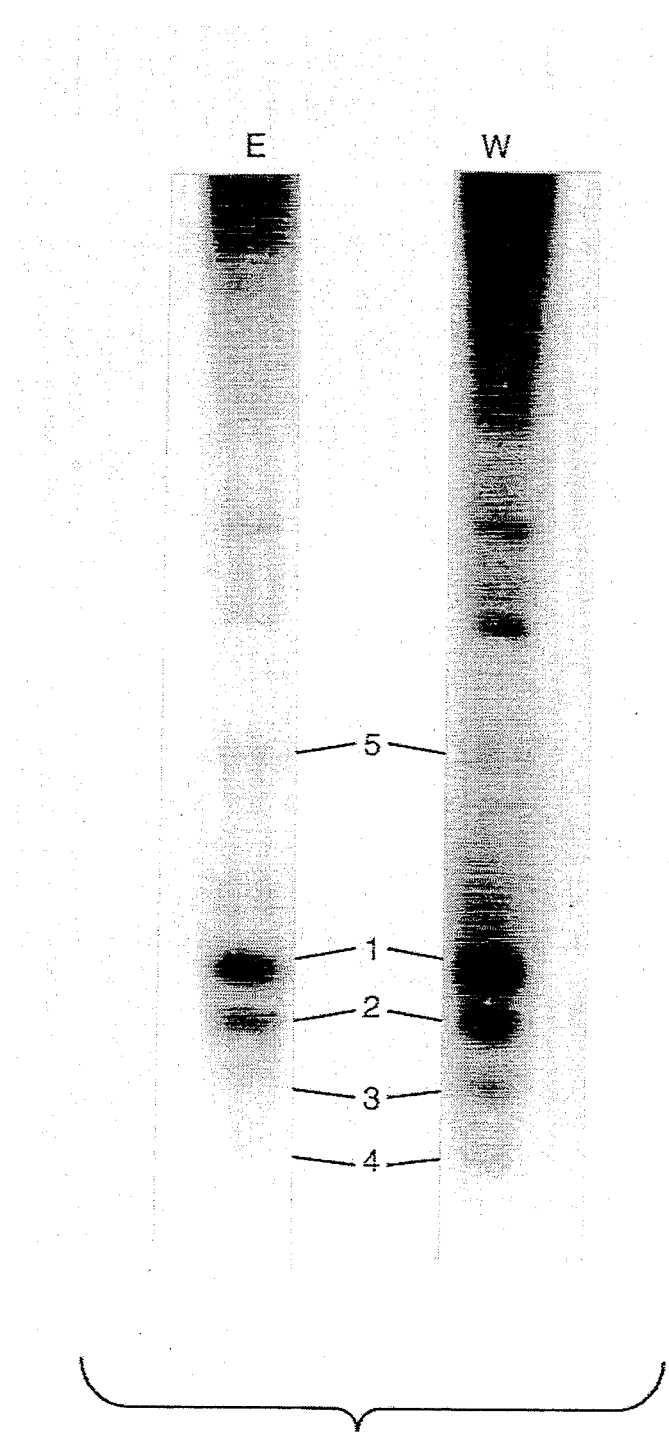
FIG._5

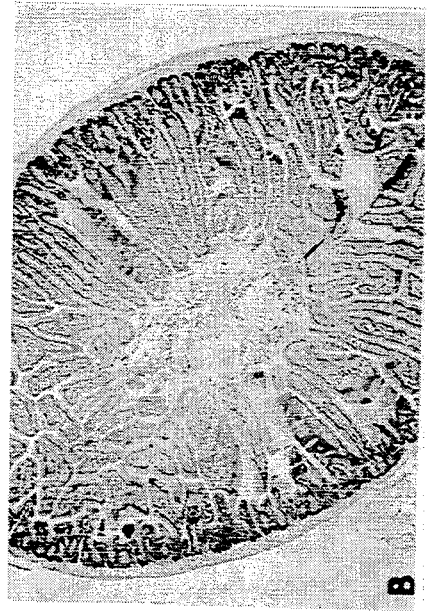
FIG._6B
FIG._6D
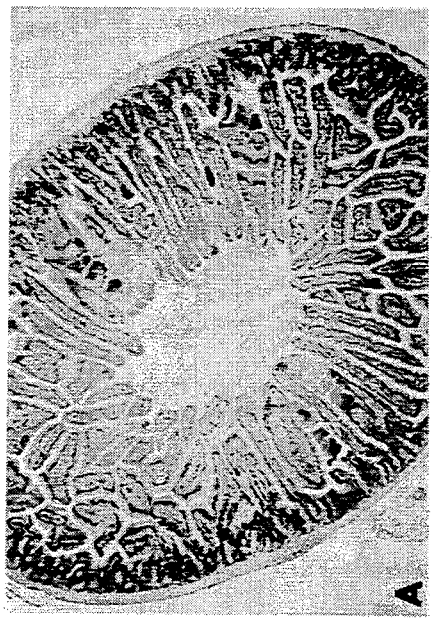
FIG._6A
FIG._6C

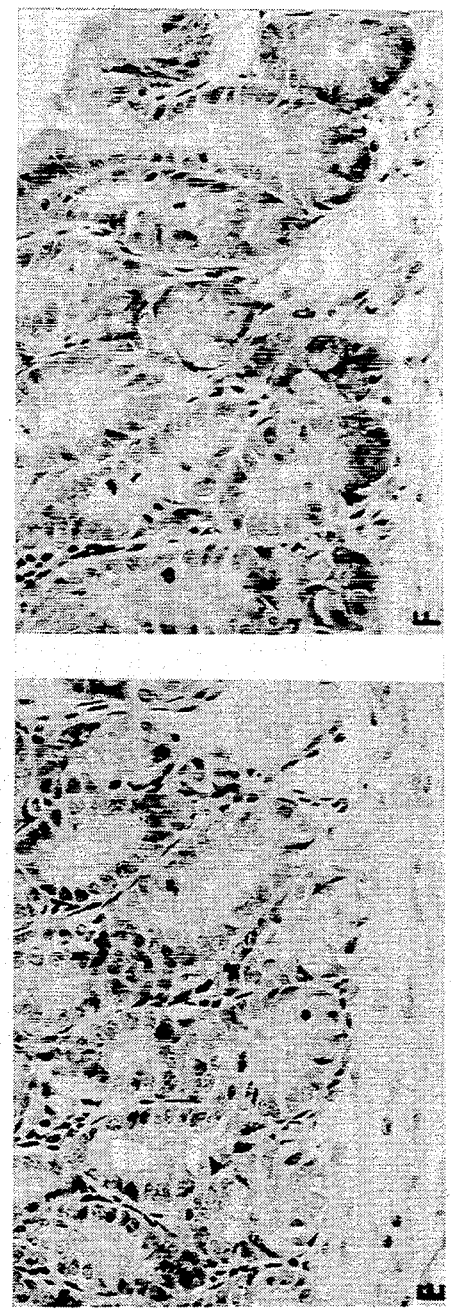
FIG._6F
FIG._6E

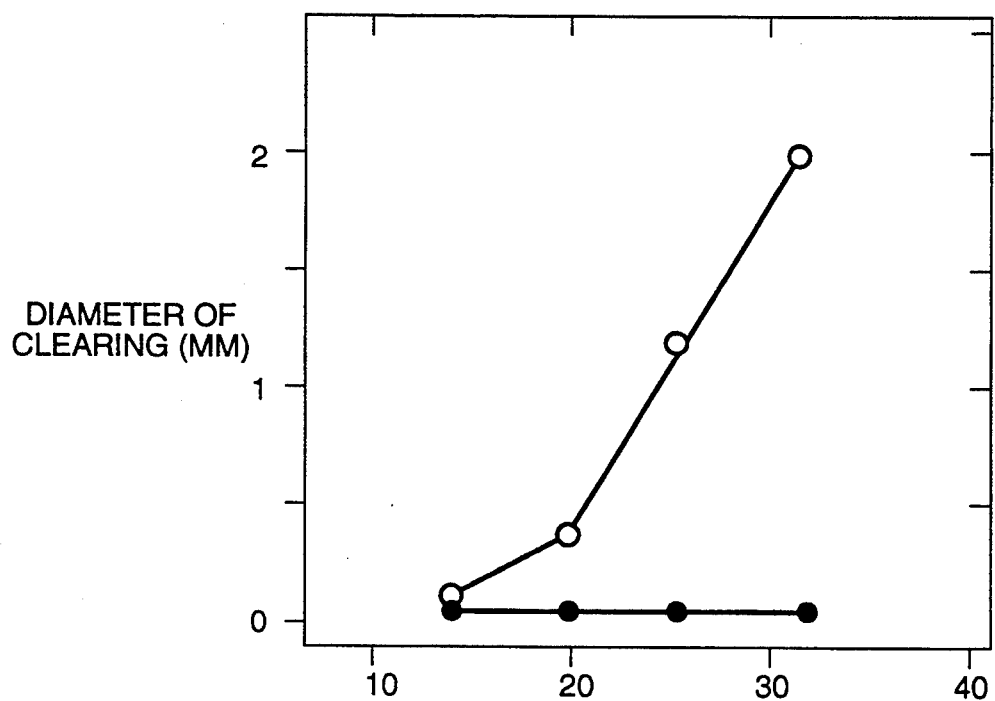
FIG._7A
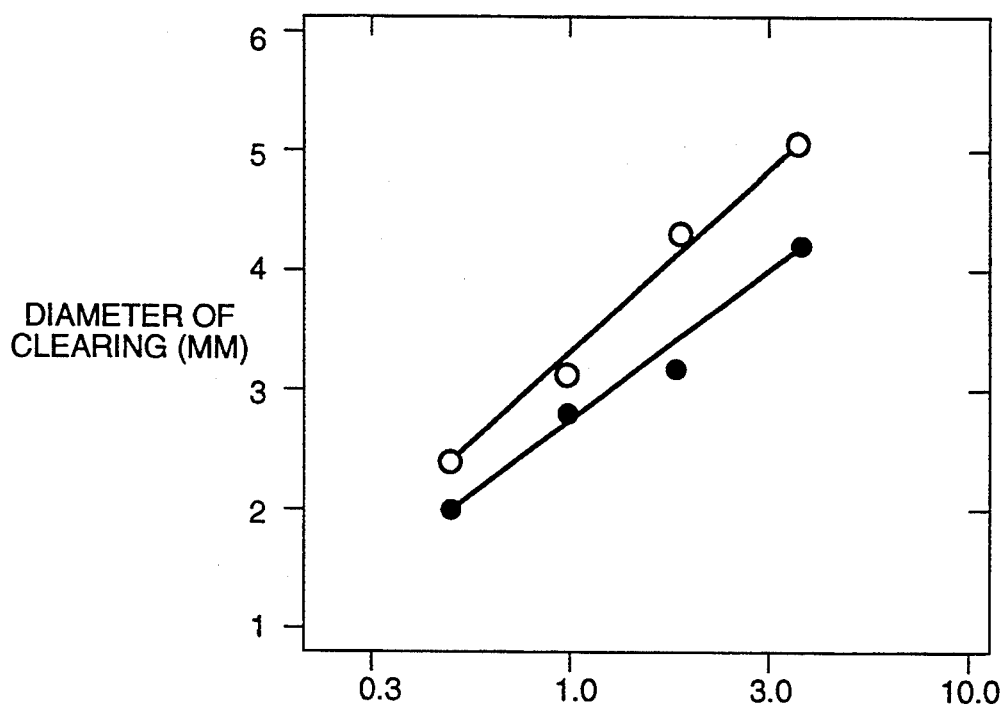
FIG._7B

5,422,424

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:1:

Leu  Arg  Asp  Leu  Val
  1                    5

( 2 ) INFORMATION FOR SEQ ID NO:2:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:2:

Leu  Ser  Lys  Lys  Leu  Ile
  1                    5

( 2 ) INFORMATION FOR SEQ ID NO:3:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:3:

Gly  Ile  Arg  Phe  Leu  Tyr
  1                    5

( 2 ) INFORMATION FOR SEQ ID NO:4:

( i ) SEQUENCE CHARACTERISTICS:

(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:4:

Arg Asn Leu Phe Leu Thr Phe Val Phe
1               5

(2) INFORMATION FOR SEQ ID NO:5:

(i) SEQUENCE CHARACTERISTICS:
(A) LENGTH: 10 amino acids
(B) TYPE: amino acid
(D) TOPOLOGY: linear (ii) MOLECULE TYPE: peptide (xi) SEQUENCE DESCRIPTION: SEQ ID NO:5:

Arg Pro Gly Leu Phe Ile Lys Arg Lys Ile
1               5                   10

(2) INFORMATION FOR SEQ ID NO:6:

(i) SEQUENCE CHARACTERISTICS:
(A) LENGTH: 9 amino acids
(B) TYPE: amino acid
(D) TOPOLOGY: linear (ii) MOLECULE TYPE: peptide (ix) FEATURE:
(A) NAME/KEY: Modified-site
(B) LOCATION: one-of(6)
(D) OTHER INFORMATION: /note="X=L OR M"

(xi) SEQUENCE DESCRIPTION: SEQ ID NO:6:

Arg Lys Gly His Leu Xaa Tyr Thr Leu
1               5

(2) INFORMATION FOR SEQ ID NO:7:

(i) SEQUENCE CHARACTERISTICS:
(A) LENGTH: 7 amino acids
(B) TYPE: amino acid
(D) TOPOLOGY: linear (ii) MOLECULE TYPE: peptide (xi) SEQUENCE DESCRIPTION: SEQ ID NO:7:

Ile Gln Gln Trp Thr Pro Gly
1               5

(2) INFORMATION FOR SEQ ID NO:8:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:8:

Leu Ser Lys Lys
1

(2) INFORMATION FOR SEQ ID NO:9:

(i) SEQUENCE CHARACTERISTICS:
(A) LENGTH: 35 amino acids
(B) TYPE: amino acid

-continued ( D ) TOPOLOGY: linear ( i i ) MOLECULE TYPE: peptide ( x i ) SEQUENCE DESCRIPTION: SEQ ID NO:9:

```
Leu  Arg  Asp  Leu  Val  Cys  Tyr  Cys  Arg  Ser  Arg  Gly  Cys  Lys  Gly  Arg
1              5                        10                       15
Glu  Arg  Met  Asn  Gly  Thr  Cys  Arg  Lys  Gly  His  Leu  Leu  Tyr  Thr  Leu
              20                       25                       30
Cys  Cys  Arg
          35
```

( 2 ) INFORMATION FOR SEQ ID NO:10:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Leu  Arg  Asp  Leu  Val  Cys  Tyr  Cys  Arg  Thr  Arg  Gly  Cys  Lys  Arg  Arg
1              5                        10                       15
Glu  Arg  Met  Asn  Gly  Thr  Cys  Arg  Lys  Gly  His  Leu  Met  Tyr  Thr  Leu
              20                       25                       30
Cys  Cys  Arg
          35
```

( 2 ) INFORMATION FOR SEQ ID NO:11:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Leu  Arg  Asp  Leu  Val  Cys  Tyr  Cys  Arg  Lys  Arg  Gly  Cys  Lys  Arg  Arg
1              5                        10                       15
Glu  Arg  Met  Asn  Gly  Thr  Cys  Arg  Lys  Gly  His  Leu  Met  Tyr  Thr  Leu
              20                       25                       30
Cys  Cys  Arg
          35
```

( 2 ) INFORMATION FOR SEQ ID NO:12:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Gly  Leu  Leu  Cys  Tyr  Cys  Arg  Lys  Gly  His  Cys  Lys  Arg  Gly  Glu  Arg
1              5                        10                       15
Val  Arg  Gly  Thr  Cys  Gly  Ile  Arg  Phe  Leu  Tyr  Cys  Cys  Pro  Arg
              20                       25                       30
```

( 2 ) INFORMATION FOR SEQ ID NO:13:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Leu Ser Lys Lys Leu Ile Cys Tyr Cys Arg Ile Arg Gly Cys Lys Arg
1               5                   10                  15

Arg Glu Arg Val Phe Gly Thr Cys Arg Asn Leu Phe Leu Thr Phe Val
            20                  25                  30

Phe Cys Cys
        35

( 2 ) INFORMATION FOR SEQ ID NO:14:

( i ) SEQUENCE CHARACTERISTICS:
    ( A ) LENGTH: 39 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:14:

Leu Lys Gln Cys His Cys Arg Lys Phe Cys Arg Pro Tyr Glu Lys Ala
1               5                   10                  15

Glu Gly Ser Cys Arg Pro Gly Leu Phe Ile Lys Arg Lys Ile Cys Cys
            20                  25                  30

Ile Gln Gln Trp Thr Pro Gly
        35

ANTIBIOTIC CRYPTDIN PEPTIDES AND METHODS OF THEIR USE

This invention was made with government support under grant number AI-22931, awarded by National Institutes of Health. The Government has certain rights in the invention.

This application is a continuation-in-part of U.S. Ser. No. 07/889,020, filed May 26, 1992 and now abandoned.

BACKGROUND OF THE INVENTION

This invention relates to antimicrobial peptides and, more specifically, to cryptdin peptides and their uses.

Survival in a world teaming with microorganisms depends on a network of host defense mechanisms. Among these mechanisms are phagocytosis in which cells which circulate in the blood system, ingest and digest potentially harmful microbes. Although pathogenic microbes may vary considerably, phagocytes are able to destroy the vast majority by sequestering them in intracytoplasmic vacuoles and exposing them to a lethal mixture of organic and inorganic toxins.

Perhaps the most remarkable ultrastructural feature of phagocytes are their several thousand cytoplasmic granules, which are membrane-bound organelles typically about 0.3 μm in diameter. During phagocytosis, some of these granules fuse to phagocytic vesicles thus enabling the contents of the granule to enter the lumen of the vesicle. Early observers surmised correctly that the granules contained factors which were responsible for intraphagosomal killing in digestion of microbes. These granules contain a mixture of antimicrobial molecules including various peptides such as the so-called defensins.

Defensins are abundant antimicrobial peptide components of vertebrate neutrophil and macrophage granules. Members of the defensin family have been identified previously in human, rabbit, guinea pig, and rat phagocytes, primarily those phagocytes termed phagocytic granulocytes. Defensins are cationic peptides, generally between 3 and 4 kD in size which exhibit broad-range antimicrobial activities against gram negative and gram positive bacteria, many fungi, and some enveloped viruses. The peptides are characterized by eight invariant amino acids including six invariant cysteine residues which constitute a unique disulfide motif. The three disulfides stabilize a tertiary conformation consisting predominantly of beta-sheet. The highly ordered structure and the absence of helix make defensins unique among known antimicrobial peptides. It appears that defensins exert their antibacterial effect by permeabilizing the cytoplasmic membrane of the target microorganism by a mechanism that may involve the formation of ion channels.

Until recently, defensins had been identified only from circulating or tissue phagocytes of myeloid origin. However, it has been surmised that similar peptides might be present in the epithelial cells of the small intestine, based on the presence of a particular mRNA. Because of the importance of the small intestine in preventing access to the systemic circulation, peptides whose activity would be effective in the small intestine, either within the cells of the epithelium or in the intestinal lumen, could provide an important therapeutic or prophylactic mechanism. The present invention provides such peptides, allowing such treatment, and providing additional benefits as well.

SUMMARY OF THE INVENTION

The present invention provides substantially purified cryptdin peptides having a consensus amino acid sequence as follows:

$X_1$-C-$X_2$-C-R-$X_3$-C-$X_4$-E-$X_5$-G-$X_6$-C-$X_7$-C-C-$X_8$ wherein $X_1$ is 3–6 amino acids, preferably chosen from LRDLV (SEQ ID NO: 1), LSKKLI (SEQ ID NO: 2), GLL or LKQ; $X_2$ is one amino acid, preferably Y or H; $X_3$ is 2 or 3 amino acids, preferably KF, KGH or *RG, where * is S, T, K or I; $X_4$ is three amino acids, preferably KGR, RPY or KR*, where * is R or G; $X_5$ is three amino acids, preferably RMN, KAE or RV*, where * is R or F; $X_6$ is one amino acid, preferably T or S; $X_7$ is 6 to 10 amino acids, preferably GIRFLY (SEQ ID NO: 3), RNLFLTFVF (SEQ ID NO: 4), RPGLFIKRKI (SEQ ID NO: 5) or RKGHL*YTL (SEQ ID NO: 6), where * is L or M; and $X_8$ is 0 to 7 amino acids, preferably R, PR or IQQWTPG (SEQ ID NO: 7).

Alternatively, the present invention provides substantially purified cryptdin peptides having a consensus amino acid sequence as follows:

$X_1$-L-$X_2$-C-Y-C-R-$X_3$-C-K-$X_4$-E-R-$X_5$-G-T-C-$X_6$-C-C-$X_7$ wherein $X_1$ is one to four amino acids, more preferably chosen for the sequences LRD, LSKK (SEQ ID NO: 8) or G; $X_2$ is one amino acid, preferably V, L or I; $X_3$ is three amino acids, KGH, or *RG where * is S, T, K or I; $X_4$ is two amino acids, preferably selected from the groups GR, RR or RG; $X_5$ is two amino acids, preferably chosen from the sequences MN, VR or VF; $X_6$ is six to nine amino acids, preferably GIRFLY (SEQ ID NO: 3) or RNLFLTFVF (SEQ ID NO: 4) or RKGHL*YTL (SEQ ID NO: 6), where * is L or M; $X_7$ is zero to seven amino acids, preferably containing an R.

In certain embodiments, the cryptdins have amino acids selected from the group consisting of the following sequences:

LRDLVCYCRSRGCKGRERMNGTCRKGH-LLYTLCCR (SEQ ID NO: 9)
LRDLVCYCRTRGCKRRERMNGTCRKGH-LMYTLCCR (SEQ ID NO: 10)
LRDLVCYCRKRGCKRRERMNGTCRKGH-LMYTLCCR (SEQ ID NO: 11)
GLLCYCRKGHCKRGERVRGTCGIR-FLYCCPR (SEQ ID NO: 12)
LSKKLICYCRIRGCK-RRERVFGTCRNLFLTFVFCC (SEQ ID NO: 13)
LKQCHCRKFCRPYEKAEGSCRPGLFIKR-KICCIQQWTPG. (SEQ ID NO: 14)

In another embodiment, the inventions provide cryptdin analogs devoid of amino acids to the N-terminal of the first cysteine.

Cryptdins are typically characterized by being naturally found in the epithelial cells of the small intestine, being cationic, being between 30 and 40 amino acids in length, having 3 to 6 amino acids to the N-terminal of the first cysteine residue, exhibiting specific antimicrobial activity against intestinal pathogens and opportunistic pathogens and being relatively non-toxic to cells of the host organism. However, there may be diversity in these structural and functional characteristics.

The present invention provides a method for detecting inflammatory pathologies in the subject by determining the amount of cryptdin in a biological sample from the subject and comparing said amount to the mean amount in normal subjects, wherein a significant deviation from the normal level is indicative of inflammatory pathology. Such significant deviation is probably between 1.0 and 2.0 standard deviations above or below the mean, preferably 1.5 standard deviations therefrom. Such a diagnostic method can be used to determine the presence of inflammatory bowel disease, pancreatitis, malignancy, infection or ileitis.

Further, the invention provides a method for treating an infectious process of the small intestine or other organ of the patient by administering cryptdin in a physiologically acceptable medium. Such treatment is particularly advantageous in patients who are immunocompromised such as from malnutrition, radiation burns, immunosuppressive infections, autoimmune disease, neonatality, bone marrow transplantation or chemotherapy. Cryptdin can be administered orally, by nasogastric intubation, by transabdominal catheter, intravenously, or by aerosol inhalation. When administered orally, it is preferably in a delayed release formulation designed to permit release in the small intestine. Cryptdin is administered in a physiologically acceptable medium, and more than one cryptdin can be administered simultaneously or sequentially.

BRIEF DESCRIPTION OF THE DRAWINGS

FIG. 1 provides the consensus structures of mouse cryptdins 1-5 and rat cryptdin-1 (SEQ ID NO: 9 to SEQ ID NO: 14 respectively). Amino acid residues are indicated by single-letter code. Dashed lines are included in mouse cryptdin-4 and rat cryptdin-1 in order to preserve the consensus sequence where these peptides are shorter than other cryptdins. Invariant residues in the enteric cryptdin peptides are boxed. Disulfide bonding motifs are depicted by connecting double lines.

FIGS. 2A to 2C show a chromatogram representing the purification of enteric cryptdins. (A) Acid extract of jejunum and ileum was chromatographed in 30% acetic acid on a P-60 column. (B) Fractions indicated by the bracket (panel A) were pooled and rechromatographed on the P-60 column. (C) Cryptdin containing fractions (bracket, panel B) were pooled and further purified by RP-HPLC on 0.46×25 cm Vydac C-18 column. Water-acetonitrile gradient elution (—) using 0.13% (vol/vol) HFBA as modifier was used to purify cryptdins 1-5. The brackets indicate the peptide contained in each peak, and the portion of each which was subjected to a second round of RP-HPLC.

FIG. 3 shows acid-urea PAGE of purified enteric cryptdins. Samples of low molecular weight enteric peptides obtained by P-60 gel filtration (FIG. 2, [panel B]) and purified cryptdins were electrophoresed on a 12.5% acid-urea gel and stained with formalin-containing Coomassie Blue. Lane A: approximately 20 μg P-60 low molecular weight peptide fractions; lanes B-F: 1 μg each of cryptdins 1-5, respectively.

FIG. 4 compares mouse cryptdins 1-5 and partially purified luminal peptides. (A) Lyophilized luminal lavage of small intestine from 12 mice was fractionated by P-60 gel filtration and electrophoresed on an acid-urea acrylamide gel (20 μg; lane 2) along side a similarly prepared sample of bowel tissue (20 μg; lane 1). The positions of cryptdins 1-5 are indicated. (B) Partially purified luminal peptides (20 μg; same material as in lane 2) were electrophoresed in a second acid-urea gel (lane 3) along with an identical sample previously treated with performic acid (lane 4). In lane 4, rapidly migrating, cyst(e)ine-containing peptides are absent due to the increased net negative charge resulting from the conversion of cyst(e)ines to cysteic acid residues.

FIG. 5 shows the identification of mouse cryptdins 1-5 in small intestine epithelium. Acid extracts of intact, whole small intestine (W) or epithelial sheets (E) were lyophilized, dissolved in sample solution and resolved on a 12.5% acid-urea acrylamide gel. Cryptdins 1-5 are identified numerically.

FIGS. 6A to 6F show the immunohistochemical localization of cryptdin-1 in small intestine. Full thickness sections of adult mouse jejunem were incubated with preimmune (FIGS. 7A, 7C, 7E) or anti-cryptdin-C rabbit IgG (FIGS. 6B, 6D, 6F) and developed using peroxidase anti-peroxidase secondary antibody magnifications: FIGS. 6A and 6B, 40X; FIGS. 6C and 6D, 250X; FIGS. 6E and 6F, 640X.

FIGS. 7A and 7B depict the antimicrobial activity of mouse cryptdin-1 (FIG. 7A). Samples of rabbit NP-1 (FIG. 7B) (lower panel) or purified natural mouse cryptdin-1 were dissolved in 0.01% acetic acid and pipetted into wells produced in a 0.6% agarose/0.3% tryptone plate containing $1 \times 10^6$ log phase bacterial cells. After incubation at 37° C. for 18 hours, antimicrobial activity was evaluated by measurement of the diameters of the clear zones. Closed circles denote wild-type *S. typhimurium;* open circles denote the phoP$^-$ mutant.

DETAILED DESCRIPTION OF THE INVENTION

The invention provides small peptide molecules, termed cryptdins, which express a broad range of antimicrobial activity, particularly against intestinal pathogens, and for this reason are useful antimicrobial agents. Cryptdins are isolated from the small intestine and are active both within the epithelial lining and within the lumen of the intestine. Because it is indicative of inflammatory processes, the presence of cryptdins can be utilized in the diagnosis of a wide range of inflammatory conditions.

As used herein, the term "cryptdin" or "enteric defensins" refers to peptides having generally between about 30 and 40 amino acids which contain a consensus sequence containing six cysteine residues. Illustrative sequences are provided in FIG. 1, which also indicates the invariant residues and the disulfide bonding motif. In addition, those residues which are preferably invariant are identified. Cryptdins are further characterized by their cationic charge and their broad range of antimicrobial activity. While related to leukocyte-derived defensins, cryptdins are distinguished from these other molecules by the presence of 3 to 6 amino acids N-terminal of the first cysteine molecule. Cryptdins may have C-terminal extensions as well. In addition, they are active against enteric microorganisms which can become blood-borne pathogens if the intestinal barrier is breached. Further, cryptdins are secreted from the cells in which they are produced, and, unlike leukocyte-derived defensins, are not toxic to mammalian cells.

It should be appreciated that various modifications can be made to the cryptdin amino acid sequence without diminishing the antimicrobial activity of the peptide. It is intended that peptides exhibiting such modifications, including amino acid additions, deletions or substitutions are within the scope of the invention.

Use of the phrase "substantially pure" in the present specification and claims as a modifier of peptide or protein means that the peptide or protein so designated has been separated from its in vivo cellular environment. As a result of the separation and purification, the substantially pure peptides and proteins are useful in ways that the non-separated impure peptides or proteins are not.

The cryptdin peptides of the present invention are preferably between about 30 and 40 amino acids. They can be synthesized by methods well known in the art, such as through the use of automatic peptide synthesizers or by well-known manual methods of peptide synthesis. In addition, they can be purified from natural sources such as small intestinal epithelium of vertebrate, preferably mammalian, origin. Such epithelium can be obtained from rats, mice, or humans, for example by means well known to those skilled in the art.

For example, the intestinal epithelium was separated from the underlying basement membrane, then concentrated by centrifugation and extracted with acid. The acid extracts, which can be lyophilized, were then dissolved in acid, such as acetic acid, stirred, and centrifuged. The supernatant was concentrated and chromatographed, as on a P-60 column and eluted in 30% acetic acid. Fractions were collected and a sample of each lyophilized, redissolved in acetic acid containing urea and electrophoresed on an acrylamide gel. Protein bands were visualized with Coomassie Blue. Fractions containing cryptdins were identified by their rapid migration on acid-urea PAGE and by apparent molecular weight, of about 4 kDd. These fractions can be rechromatographed and finally purified by RP-HPLC. Amino acid sequences can be determined by means well known to those skilled in the art such as through the use of the automatic sequencer system.

Anti-cryptdin antibodies can be made by methods conventional in the art. For example, polyclonal antiserum can be raised in appropriate animals, such as rabbits, mice, or rats. Cryptdin peptides, either synthetic or obtained from natural sources, can be used to immunize the animal. Preferably an analogue such as that termed cryptdin-C, which corresponds to residues 4–35 of mouse cryptdin-1 (SEQ ID NO: 9) in FIG. 1, is used as the immunogen. The cryptdin immunogen can then be used to immunize animals by means well known to those skilled in the art. Serum samples are collected until the anti-cryptdin titer is appropriate. Various fractions of the antisera, such as IgG, can be isolated by means well known in the art. Alternatively, cryptdin immunogens can be used to obtain monoclonal antibodies, again by means well known in the art, see for example Harlow and Lane, *Antibodies: A Laboratory Manual*, (Cold Springs Harbor Laboratory, 1988).

The antimicrobial, or antibacterial, activity of cryptdins can be measured against various pathogens. Microorganisms are grown to appropriate concentration, mixed with an appropriate medium, such as an agarose-trypticase soy medium, and contacted with solutions of the cryptdins. After appropriate incubation interval, the antimicrobial activity is apparent from clear zones surrounding the antibacterial samples. The clear zones are concentration dependent. Anti-cryptdin antibodies can be used to determine the presence of cryptdin in biological samples, such as histological samples. For example, sections of small intestine are fixed by means well known to those skilled in the art, and incubated with anti-cryptdin antibodies such as an IgG fraction of antiserum. An appropriate detectable second antibody can then be used to identify such as by visualization, the primary antibody attached to the cryptdin. Means of detection include the use of radioactive protein A or enzyme substrates such as peroxidase.

Alternative methods of determining the presence of cryptdin, such as the determination in a biological sample, for example, material obtained from disruption of cells or tissues, can be useful to determine the presence of inflammatory processes. In the presence of inflammatory processes, the concentration of cryptdins is significantly altered from that found in the normal cell. In particular, deviations from the norm of one to two standard deviations are indicative of inflammatory processes. Such inflammatory processes can include, for example, inflammatory bowel disease, pancreatitis, malignancy, infection, or ileitis.

Because of their broad range of antimicrobial activity, and their ability to function within the intestinal epithelium and/or lumen, cryptdins are potent therapeutic agents for infections of the intestine. In particular, cryptdins are useful in situations where the subject is immunocompromised, such as those having been subjected to malignancy, malnutrition, chemotherapy, radiation, immunosuppressive viruses, autoimmune disease or neonatality. In addition, cryptdins are useful in surgical prophylaxis, for example, by functioning to help sterilize the small bowel. Cryptdin, either purified from natural sources or synthetic, can be administered to a subject in need of such therapy by various means, including oral administration, preferably in a slow-release type formulation which will avoid release within the stomach. Alternatively, cryptdins can be administered through nasogastric intubation, transabdominal catheter, intravenously or aerosol administration. Individual species of cryptdin can be administered singly or a combination can be administered simultaneously or sequentially. Administration of cryptdins is repeated as necessary.

Prior to the characterization of a mouse intestinal defensin cDNA, expression of defensins was thought to be limited to professional phagocytes, i.e., neutrophils and macrophages. The presence of high levels of cryptdin MRNA in Paneth cells has led to the hypothesis that defensins synthesized in intestinal epithelium may contribute to antimicrobial barrier function in the small bowel (Ouellette et al., *J. Cell Biol.* 108:1687–1695 (1989a)). Isolation and characterization of five mouse cryptdin peptides and one rat cryptdin peptide, and the demonstration of antibacterial activity of the most abundant mouse peptide, mouse cryptdin-1, provides additional evidence for the antimicrobial role of defensins in the small intestine. The immunohistochemical localization of cryptdin(s) to Paneth cells is consistent with previous in situ hybridization analysis and suggests that defensins produced by these cells may contribute to restricting the colonization and invasion of the small bowel by bacteria.

Initial efforts to purify intestinal defensins focused on the isolation of mouse cryptdin-1, the peptide predicted from the cryptdin cDNA sequence. Since the deduced peptide is highly cationic, intestinal peptides were solubilized by homogenizing intact mouse jejunum and ileum in 30% formic acid. Acid-urea PAGE of the crude extract revealed several bands with $R_f$ values similar to those of rabbit defensin NP-1 and cryptdin C, a folded synthetic defensin congener corresponding to residues 4 to 35 in cryptdin-1 (SEQ ID NO: 9). Peptides corresponding to these bands were purified approximately 200-fold by sequential gel filtration chromatography on Bio-Gel P-60 (FIGS. 2A and 2B). Electrophoresis of P-60 column fraction samples on acid-urea gels showed that five fractions eluting between two prominent peaks (FIG. 2A & 2B, brackets) contained putative cryptdin peptides (FIG. 3, lane a). Peptides in these P-60 fractions migrated with $M_r$s of approximately 4 kDal on SDS-PAGE (data not shown), consistent with the molecular weight of defensins. Furthermore, treatment of P-60 fraction samples with performic acid reduced the electrophoretic mobility of the five putative mouse cryptdins in acid-urea gels, behavior that is characteristic of defensins and polypeptides that contain multiple cysteine residues.

Defensins in pooled P-60 fractions were purified further using sequential rounds of RP-HPLC utilizing different ion-pair agents. Initial HPLC fractionation utilized water-acetonitrile gradients containing 0.13% heptafluorobutyric acid (HFBA) as the ion-pairing agent, whereby each of the five peptides contained in the pooled P-60 fractions was resolved to near purity in a single run (FIG. 2, bottom panel). Complete purification of five peptides, mouse cryptdins 1-5, was achieved by subsequent RP-HPLC using 0.1% trifluoroacetic acid (TFA) (FIG. 3, lanes B-F). Assuming extraction of individual peptides is equally efficient, both acid-urea gel electrophoresis and RP-HPLC of the P-60 fractions containing putative cryptdins showed that the relative abundance of the peptides is cryptdin-1>cryptdin-2>cryptdin-5>cryptdin-3>cryptdin-4. The relative amounts of cryptdins 1-5 have been qualitatively reproducible in every preparation of acid-extracted protein from mouse small intestine.

Biochemical characterization of cryptdins 1-5 demonstrated that these peptides are defensins. Amino acid analysis of each peptide showed their compositions were compatible with defensin-like molecules: cationic peptides of 30 to 35 residues which included 6 half-cysteines. The complete sequences of mouse cryptdins 1-5 (SEQ ID NO: 9 to SEQ ID NO: 13, respectively) were determined by automated degradation and amino acid analysis of carboxyl terminal chymotryptic peptides. The primary structures of the five enteric defensins derived from mouse small intestine and the cryptdin derived from rat intestine contain the distinctive structural features of human, rabbit, rat and guinea pig neutrophil defensins (Lehrer et al., Cell 64:229-230 (1991a)), i.e., the six invariant cysteine residues, and glycine and glutamic acid in positions that are also highly conserved in myeloid defensins.

Mouse cryptdins 1-5 and rat cryptdin-1 contain features that are unique and distinct from defensins of myeloid origin. Mouse cryptdins 1, 2 and 3 (SEQ ID NO: 9, 10, and 11, respectively) are almost identical, differing in sequence only at position 10 (Ser, Thr, or Lys), position 15 (Gly or Arg), or position 29 (Leu or Met) as shown in FIG. 1. Analysis of codons from which these amino acid differences could arise shows that the conversion of $Ser^{10}$ to $Lys^{10}$ in cryptdins 1 and 3, respectively, requires two nucleotide substitutions. On the other hand, single nucleotide changes in cryptdin-2 could give rise both to cryptdins-1 and 3, suggesting that the cryptdin-2 gene may be an intermediate or progenitor of the cryptdin-1 and cryptdin-3 genes.

By homology with the structures of known myeloid defensins, the cryptdin-1 N-terminus had been predicted to be at $Leu^4$ or $Val^5$, 1-2 residues prior to the first conserved cysteine. However, compared to myeloid defensins, intestinal defensins have variably extended N-termini that contain from three (mouse cryptdin-4 and rat cryptdin-1) to six (mouse cryptdin-5) amino acids preceding the first cysteine. In mouse cryptdins 1-3 and 5, the N-peptidyl extensions consist of two charged internal residues flanked by amino acids with hydrophobic sidechains. Since natural variation in defensin amino termini has been shown to correlate with relative antimicrobial potency in vitro (Ganz et al., J. Clin. Invest. 76:1427-1435 (1985)), the extended N-termini of enteric defensins may have evolved for a unique role in the bowel.

Cryptdin-4, the most cathodal, and apparently least abundant, enteric defensin was the first defensin found to contain a chain length variation between the fourth and fifth cysteine residues. Unlike the majority of previously known defensins, in which nine amino acids separate the fourth and fifth cysteines (Lehrer et al., supra, 1991a), mouse cryptdin-4 (SEQ ID NO: 12) contains only six residues between the same two amino acids (FIG. 1). In addition, rat cryptdin-1 (SEQ ID NO: 14) contains ten amino acid residues between the fourth and fifth cysteines. These findings indicate the defensin fold involving this stretch of the peptide chain can accommodate significant variability in the size of the loop, as compared to the invariant loop size defined by crystal and NMR structures, respectively, of human and rabbit neutrophil defensins. Also, rat cryptdin-1 (SEQ ID NO: 14) is the only cryptdin containing three, instead of four, amino acid residues between the second and third cysteine residues.

Since cryptdin mRNA levels increase during postnatal development of mouse small bowel (Ouellette et al., supra, 1989a), it was investigated whether accumulation of enteric defensins was regulated similarly. Analysis of intestinal acid extracts from male and female mice showed that mouse cryptdins 1-3 & 5 are present in adult mice, regardless of gender. On the other hand, extracts from 9 day-old mice lack the peptides, consistent with postnatal accumulation of cryptdin MRNA.

Mouse cryptdins 1-5 derive from intestinal epithelial cells. In the presence of EDTA, the intestinal epithelium no longer adheres to the underlying basement membrane and floats free of the lamina propria upon gentle agitation (Bjerknes and Cheng, Am. J. Anat. 160:51-63 (1981)). Preparations of epithelial sheets isolated in this manner were concentrated by low-speed centrifugation and extracted with 30% formic acid. Peptides extracted from isolated epithelial sheets co-migrate with cryptdins 1-5 when analyzed by acid-urea PAGE (FIG. 5), demonstrating their epithelial origin.

Immunoperoxidase staining of full-thickness sections of small intestine with an anti-cryptdin antibody demonstrate cryptdin antigen in Paneth cells, consistent with localization of cryptdin mRNA by in situ hybridization (Ouellette et al., supra, (1989a)). Incubation of sections of adult mouse jejunum and ileum with a polyclonal anti-cryptdin IgG produced by rabbits immunized with the synthetic congener cryptdin-C localized the immunoperoxidase reaction to granulated cells, morphologically defined as Paneth cells, at the base of every crypt (FIGS. 6A-6F). The staining pattern accentuates the granular appearance of the cytoplasm in these cells, and the immunoreactivity appears to be particularly strong over Paneth cell granules. The antibody is specific for mouse cryptdin(s), since it is negative both for rat and human Paneth cells (data not shown). Leukocytes in the lamina propria of the villi also were negative, suggesting that related enteric defensins are not expressed by phagocytes or lymphocytes. Because of the extensive similarity of mouse cryptdins 1-3 (FIG. 1), the polyclonal antibody produced against cryptdin-C probably recognizes the three peptides. Conversely, because mouse cryptdins 4 and 5 differ markedly from cryptdins 1-3, the anti-cryptdin-C antibody is unlikely to react with cryptdins 4 and 5, leaving their origin in Paneth cells somewhat unresolved.

Immunohistochemical data suggest cryptdins are secreted into the intestinal lumen. Material in the small intestinal lumen is strongly positive for the antibody but negative for pre-immune sera or IgG (FIGS. 6A & 6B). Although the agonist for Paneth cell defensin secretion is unknown, lysozyme, another protein constituent of Paneth cell granules, is secreted into the lumen under cholinergic regulation. Consistent with immunochemical detection of anti-cryptdin-C positive material in the intestinal lumen, acid-urea PAGE of saline washes of adult jejunum and ileum detect the presence of peptides with mobilities very similar to but distinct from the mobility of cryptdins (FIG. 4). Nevertheless, the peptides are not identical to cryptdins 1-5 by either migration in acid-urea PAGE or by HPLC analysis, suggesting they may correspond to cryptdins that have been processed further. Conceivably, luminal cryptdin or cryptdin-like material could derive from exfoliated Paneth cells in the lumen, but the low rate of Paneth cell turnover suggests this is unlikely. The release of cryptdins or processed variants into the small bowel by Paneth cells contrasts with the apparent lack of defensin secretion by leukocytes, and it is inferred that a secretory pathway may exist for the constitutive delivery of defensins into the intestinal lumen by Paneth cells.

The antibacterial activity of purified mouse cryptdin-1, the most abundant mouse enteric defensin, was tested against wild-type and phoP mutant *S. typhimurium* using a modified plate diffusion assay (Lehrer et al., *J. Immunol. Methods* 137:167-173 (1991b)). phoP is a two-component regulatory locus that is essential to *S. typhimurium* virulence and survival within macrophages (Fields et al., *Science* 243:1059-1062 (1989), Miller et al., *Proc. Natl. Acad. Sci. USA* 86:5054-5058 (1989)), and mutants in the locus are particularly sensitive to rabbit defensins NP-1 and NP-2 when compared to wild-type parent strains (Fields et al. supra, Miller et al., *Infect. Immun.* 58:3706-3710, (1990)). Under the assay conditions described, the antimicrobial activity of rabbit defensin NP-1 against wild-type and the phoP mutant organisms are quite similar (FIG. 7B)7. On the other hand, at concentrations of mouse cryptdin-1 that are effective against the attenuated mutant, wild-type *S. typhimurium* is completely resistant to the effects of the peptide (FIG. 7A). The differential activity of cryptdin-1 against avirulent *S. typhimurium* suggests that resistance to mucosal defensins may be of particular importance for the evolution of virulence in enteric pathogens.

References are cited throughout the specification. These references in their entirety are incorporated by reference into the specification to more fully describe the state of the art to which it pertains.

The following examples are intended to illustrate but not limit the invention.

EXAMPLE I

Purification of Enteric Defensins

Outbred Swiss mice [(Crl:CD-1)(ICR)BR], 45-day-old males (30-35 g) or timed-pregnant dams, were obtained from Charles River Breeding Laboratories, Inc. (North Wilmington, Mass.). In studies of newborn mice, litters were culled to 8 pups within 12 hours of delivery. Mice were housed under 12-hour cycles of light and darkness and had free access to food and water.

Jejunum and ileum were removed intact from mice killed by cervical dislocation. Intestinal lumens of individual mice were rinsed with 35 ml PBS, and washes were acidified by addition of 3.5 ml glacial acetic acid and frozen. After washing, intestines of individual mice were disrupted thoroughly in 35 ml ice-cold 30% formic acid using a Polytron homogenizer (Brinkmann Instruments, Westbury, N.Y.). Homogenates were stirred continuously for 18 hours at 4° C., clarified by centrifugation at 27,000 rpm in the SW28.1 rotor for 30 minutes at 4° C. lyophilized, and stored at −85° C.

Sheets of intestinal epithelium were isolated by EDTA perfusion (Bjerknes and Cheng, supra). After irrigation of the intestinal lumen, anesthetized mice were perfused systemically with 30 mM EDTA in $Ca^{++}/Mg^{++}$-free Hank's by left ventricular injection. Epithelial sheets were separated from basement membrane of the underlying lamina propria by gentle shaking of the exerted intestine in ice-cold $Mg^{++}$-free Hank's buffer. Under these conditions, sheets of pure intestinal epithelium released from the lamina propria and were concentrated by centrifugation. Cells deposited by low-speed centrifugation were homogenized as before in 10 ml 30% formic acid.

Lyophilized acid extracts were dissolved in 100 ml of 30% acetic acid, stirred for 2 hours at room temperature, and clarified by centrifugation at 27,000 x g at 22° C. for 1 hour. The supernatant was concentrated to 30 ml by centrifugal evaporation and chromatographed (15 ml per loading) on a 2.5×55 cm column of Bio-Gel P-60 equilibrated in 30% acetic acid. Fractions (7.5 ml) were collected at 15 ml/hour while the effluent was continuously monitored at 280 nm. A 200 μl sample of each fraction was lyophilized, dissolved in 30 μl of 5% acetic acid containing 3.0M urea, and electrophoresed on 12.5% acid-urea acrylamide gels (Selsted & Harwig, *Infect. Immun.* 55:2281-2286 (1987)). Protein bands were visualized with Coomassie R-250.

Fractions containing putative defensins were identified by acid-urea PAGE, in which the peptides migrated rapidly ($>0.6 \times R_f$ of the methyl green tracking dye) and by SDS-PAGE where the peptides had apparent of 4 kDal. These fractions were pooled, lyophilized, and dissolved in 6 ml of 30% acetic acid and rechromatographed on Bio-Gel P-60. Final purification of five enteric defensins was achieved by RP-HPLC on a 0.46× 25 cm Vydac C-18 column using HFBA and TFA as ion-pairing agents as described above.

EXAMPLE II

Peptide Characterization

Amino acid analyses were performed on 6 N HCl hydrolysates (150° C., 2 hours) of unmodified or performic-acid oxidized peptides. Hydrolysates were derivatized with phenylisothiocyanate, and the resulting phenylthiocarbamyl amino acids were quantitated as described previously (Selsted & Harwig, supra, 1987, which is incorporated herein by reference). Peptide samples were reduced with dithiothreitol and pyridylethylated with 4-vinylpyridine for sequencing (Henschen, In: Advanced Methods in Protein Microsequence Analysis, Wittmann-Liebold, B. et al. (eds), pp. 244-255

(1986)). Sequence determinations were performed by automated Edman degradation on an ABI model 477 system (Applied Biosystems, Inc., Foster City, Calif.) with on-line PTH amino acid analysis. In certain cases, the C-terminus was confirmed by amino acid analysis of tryptic peptides.

EXAMPLE III

Antimicrobial Assay

Antibacterial activity was measured in an agar diffusion assay (Lehrer et al., supra, 1991b) using wild-type *Salmonella typhimurium* (ATCC 10428) or an isogenic phoP mutant of *S. typhimurium* (strain CS015 phoP102::Tn10d-Cam, Miller et al., S. UPra, 1989). ATCC 10428 and CS015 were grown to log phase in trypticase soy broth at 37° C. harvested by centrifugation, and resuspended to $1 \times 10^7$ colony forming units (CFU) per ml in 10 mM sodium phosphate buffer (pH 7.4). A 100 μl aliquot of each organism was mixed with 10 ml of 1% agarose in 0.03% (w/v) trypticase soy medium, 10 mM sodium phosphate (pH 7.4) at 42° C. Samples (5 μl) of peptide solution were pipetted into 3 mm diameter wells formed in the agarose with a sterile punch. After 3 hours at 37° C. the inoculated agarose plate was overlayed with 1% agarose containing 6% trypticase soy medium. After 12-16 hours, antimicrobial activity was apparent as clear zones surrounding wells loaded with antibacterial samples, and zones were concentration-dependent.

EXAMPLE IV

Anti-cryptdin Antibody

A polyclonal rabbit antibody was prepared to a synthetic analogue of cryptdin-1. The peptide, termed cryptdin-C, corresponding to residues 4-35 in cryptdin-1 (FIG. 4) was synthesized by solid phase chemistry using $N^\alpha$-butoxycarbonyl protection (Kent, *Ann. Rev. Biochem.* 57:957-989 (1988)). Following cleavage/deprotection of synthetic cryptdin-C with TFA-trifluoromethanesulfonic acid, the peptide was precipitated in ethyl ether and dried in vacuo. A 100 mg sample was dissolved in 10 ml of 6.0M guanidine-HCl, 0.2M Tris-HCl, pH 8.2 containing 20 mg of DTT. The sample was purged with nitrogen, heated to 50° C. for 4 hours, diluted 100-fold with deionized water, and dialyzed exhaustively, first against 0.1M sodium phosphate (pH 8.2), 20 mM guanidine-HCl, 100 mM NaCl, then against 5% acetic acid. The sample was lyophilized, dissolved in 10 ml 5% acetic acid, and subjected to RP-HPLC on a $1 \times 25$ cm Vydac C-18 column. the earliest eluting peak, representing about 0.5% of the crude peptide was determined by amino acid analysis to have the desired composition.

A sample (1.5 mg) of cryptdin-C was supplied, without conjugation to carrier, to Berkeley Antibody Company (Berkeley, Calif.) for immunization of 2 New Zealand White rabbits. Serum samples were collected for 12 weeks, until the anti-cryptdin C titer, determined by ELISA, reached ca. 1:10,000 for each rabbit. IgG was isolated from antiserum using DEAE Econo-Pac chromatography (Bio-Rad, Richmond, Calif.) as described by the manufacturer.

EXAMPLE V

Immunohistochemistry

Paraffin sections of formalin-fixed mouse mid small bowel were deparaffinized, treated with 1.1% hydrogen peroxide for 40 minutes, washed extensively with water and then with PBS. Slides were treated for 20 minutes at 37° C. with 500 μg/ml trypsin in PBS, washed twice with PBS, and blocked by incubation for 20 minutes with 5% porcine serum. Slides were incubated for 20 minutes in rabbit anti-cryptdin IgG (1:10 dilution relative to serum IgG concentration), and washed with blocking serum. Porcine anti-rabbit IgG was used as linking reagent between the primary antibody and rabbit antiperoxidase-peroxidase conjugate (Dako Carpenteria, Calif.). Diaminobenzidine was used as peroxidase substrate, and parallel incubations were performed using equivalent dilutions of rabbit preimmune IgG as the primary antibody.

EXAMPLE VI

Fmoc Synthesis, Purification and Characterization of Cryptdin-1

Synthesis was initiated at the 0.13 mmole scale using Wang resin coupled to flourenylmethoxycarbonyl (Fmoc)-arginine via an acid labile linker. Synthesis was carried out in dimethylformamide (DMF) using (relative to resin substitution) 3-fold excess of Fmoc-amino acids activated in situ with 3-fold excess of BOP (benzotriazol-1-yl-oxy-tris (dimethylamino) phosphonium hexafluorophosphate) and HOBt (hydroxybenzotriazole), and -fold molar excess of N-methylmorpholine (Nmm). Fmoc removal during synthetic cycles was achieved using cycles of 50% and 25% piperidine in DMF. The side-chain protection scheme utilized the following Fmoc-amino acids: OtBut-aspartic acid, Pmc-arginine, tBut-tyrosine, tBut-serine, Trt-cysteine, tBoc-lysine, OtBut-glutamic acid, Trt-asparagine, tBut-threonine, and Trt-histidine.

The peptide chain was assembled in a Synostat batch synthesizer using single couplings at all additions except at leucine and valine which were double coupled. The cycle sequence is as follows:

1. Wash with DMF 4X for 2 minutes;
2. Deblock: 50% piperidine 1X for 5 minutes;
3. Deblock: 25% piperidine 1X for 15 minutes;
4. Wash with DMF 4X for 2 minutes;
5. Dissolve amino acids +BOP +HOBt in DMF and transfer to reaction vessel;
6. Add Nmm to RV and mix for 60 minutes; and
7. Wash with DMF 1X for 2 minutes After coupling of the amino terminal residue, the terminal Fmoc group was removed using the following cycle:

1. Wash with DMF 4X for 2 minutes;
2. Deblock: 50% piperidine 1X for 5 minutes
3. Deblock: 25% piperidine 1X for 15 minutes;
4. Wash with DMF 4X for 2 minutes;
5. Wash with dichloromethane 1X for 5 minutes;
6. Wash with isopropanol 4X for 5 minutes;
7. Dry under stream of $N_2$ 1X for 10-20 minutes; and
8. Dry under vacuum 1X for 12 hours.

The peptide-resin was weighed to determine mass increase. To cleave and deprotect the peptide-resin, it is first reswelled in dichlormethane. Swollen resin is then cleaved and deprotected by addition of reagent R 90% trifluoroacetic acid, 5% thioanisole, 3% ethanedithiol, 2% anisole at a ratio of 10 ml per gram peptide-resin. Cleavage/deprotection was carried out under nitrogen for 18 hours at room temperature. The cleavage mixture was separated from resin by filtration through a scintered glass funnel washed with 1-2 ml of fresh reagent R, and diluted 5-fold with 50% acetic acid. Glacial acetic acid was added to a final acetic acid concentration of 50%. This solution was extracted three times with 0.33 volumes of methylene chloride. The aqueous phase was lyophilized to dryness, dissolved in 50% acetic acid and relyophilized. This was repeated 3 to 4 times. The dry peptide was dissolved in 30% acetic acid at a concentration of 20 mg/ml, and passed over an 800 ml Sephadex G-10 column equilibrated in 30% acetic acid. Peptide-containing fractions were pooled, lyophilized, dissolved in 5% acetic acid, then diluted ten-fold with water to a final protein concentration of ca. 1 mg/ml. The pH of the solution was adjusted to 8.0 with ammonium hydroxide, and mixed rapidly with a magnetic stirrer at room temperature in a beaker open to room air. The solution pH was adjusted periodically to 8.0 over a period of 4 days. The solution was then acidified with acetic acid to pH 3.5 and then lyophilized.

C-18 reverse-phase HPLC using 0.1% TFA-water/acetonitrile gradients was used to purify the folded peptide. Fractions were analyzed on acid-urea gels and compared to natural cryptdin-1. The yield from an initial crude peptide preparation of 500 mg was approximately 30 mg.

Characterization of Synthetic Cryptdin-1.

Synthetic cryptdin-1 has been compared to natural peptide on analytical RP-HPLC, SDS-PAGE, and under three different conditions on acid-urea PAGE. For analysis on acid-urea PAGE, peptide was electrophoresed without modification, after reduction with dithiothreitol, or after performic acid oxidation. Under all conditions described, native and synthetic cryptdin-1 behaved identically. Finally, the amino acid compositions of natural and synthetic cryptdin-1 were also indistinguishable.

Although the invention has been described with reference to the disclosed embodiments, it should be understood that various modifications can be made without departing from the spirit of the invention. Accordingly, the invention is limited only by the following claims.

---

We claim:

1. A substantially purified cryptdin peptide of enteric origin having an amino acid sequence selected from the group consisting of:

LRDLVCYCRSRGCKGRERMNGTCRKGH-LLYTLCCR (SEQ ID NO: 9)
LRDLVCYCRTRGCKRRERMNGTCRKGH-LMYTLCCR (SEQ ID NO: 10)
LRDLVCYCRKRGCKRRERMNGTCRKGH-LMYTLCCR (SEQ ID NO: 11)
GLLCYCRKGHCKRGERVRGTCGIR-FLYCCPR (SEQ ID NO: 12)
LSKKLICYCRIRGCK-RRERVFGTCRNLFLTFVFCC (SEQ ID NO: 13) and
LKQCHCRKFCRPYEKAEGSCRPGLFIKR-KICCIQQWTPG (SEQ ID NO:14).

* * * * *

UNITED STATES PATENT AND TRADEMARK OFFICE
CERTIFICATE OF CORRECTION

PATENT NO. : 5,422,424
DATED : June 6, 1995
INVENTOR(S) : Selsted et al.

It is certified that error appears in the above-indentified patent and that said Letters Patent is hereby corrected as shown below:

In column 4, line 14, please delete "FIGS. 7A, 7C, 7E)" and replace therefor with --FIGS. 6A, 6C, 6E)--.

In column 9, line 49, please delete the additional 7 after "(FIG. 7B)".

In column 10, line 49, please insert --$M_r$s-- after "apparent" and before "of 4 kDal.".

In column 11, line 14, please delete "S. UPra," and replace therefor with --supra--.

In column 12, line 28, between "and" and "-fold" please insert --6--.

Signed and Sealed this

Twentieth Day of May, 1997

Attest:

BRUCE LEHMAN

Attesting Officer

Commissioner of Patents and Trademarks